United States Patent [19]

Sedergran

[11] Patent Number: 5,008,399
[45] Date of Patent: Apr. 16, 1991

[54] DIASTEREOSELECTIVE PREPARATION OF PHOSPHINATE ESTERS

[75] Inventor: Thomas C. Sedergran, Plainsboro, N.J.

[73] Assignee: E. R. Squibb & Sons, Inc., Princeton, N.J.

[21] Appl. No.: 467,451

[22] Filed: Jan. 19, 1990

[51] Int. Cl.$^5$ .................... C07B 53/00; C07F 9/572; C07F 9/32
[52] U.S. Cl. .................................. 548/413; 558/107
[58] Field of Search .................. 548/413; 558/107

[56] References Cited

U.S. PATENT DOCUMENTS

| | | | |
|---|---|---|---|
| 4,337,201 | 6/1982 | Petrillo, Jr. | 548/413 |
| 4,384,123 | 5/1983 | Petrillo, Jr. | 548/409 |
| 4,873,356 | 10/1989 | Petrillo, Jr. et al. | 558/180 |

OTHER PUBLICATIONS

Crilley, Tet. Letters 30, 885–8 (1989).
Jaeger, Chem. Abs. 90, 134487 (1979).
Ohtauka et al., "New Condensing Reagents For Stereospecific Synthesis of Dinucleoside Monophosphate Aryl Esters", Tetrahedron Letters, vol. 22, No. 45, p. 4483–4486 (1981).

*Primary Examiner*—Mark L. Berch
*Attorney, Agent, or Firm*—Stephen B. Davis

[57] ABSTRACT

An increase in the disastereoselectivity resulting from the reaction of a phosphinic acid ester of the formula

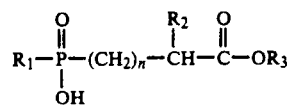

with the halo ester of the formula

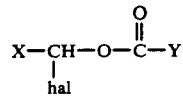

is achieved by carrying out the reaction in the presence of 4-methylmorpholine, diazabicyclooctane, quinuclidine, 1-methylpyrolidine, or cinchonidine. After removal of the $R_3$ protecting group and fractional crystallization, the resulting desired diastereomeric pair can be resolved, and the desired isomer can be coupled to 4-substituted L-proline to give compounds possessing angiotensin converting enzyme inhibition activity. In particular, the process is useful in producing the antihypertensive agent fosinopril sodium in increased yields.

11 Claims, No Drawings

DIASTEREOSELECTIVE PREPARATION OF PHOSPHINATE ESTERS

BACKGROUND OF THE INVENTION

Fosinopril sodium, [1[S*(R*)], 2α,4β]-4-cyclohexyl-1-[[[2-methyl-1-(1-oxopropoxy)propoxy](4-phenylbutyl)phosphinyl]acetyl]-L-proline, monosodium salt, having the structural formula

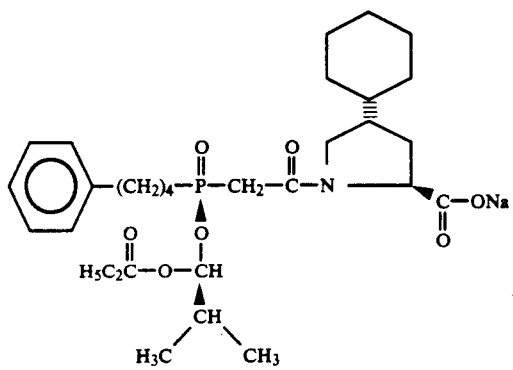

is currently being evaluated as an antihypertensive agent.

Petrillo, Jr. in U.S. Pat. Nos. 4,337,201 and 4,384,123 discloses various phosphinylalkanoyl substituted prolines having angiotensin converting enzyme inhibition activity including fosinopril.

Petrillo, Jr. et al. in U.S. Pat. No. 4,873,356 discloses a process for preparing fosinopril in which a phosphinic acid ester of the formula

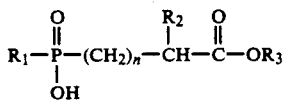

wherein $R_3$ is benzyl or substituted benzyl, n is zero or one, and $R_1$ is lower alkyl, aryl, arylalkyl, cycloalkyl or cycloalkylalkyl is reacted with a halo ester of the formula

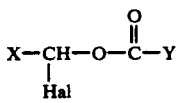

wherein Hal is Cl or Br, X is hydrogen, lower alkyl, or phenyl, and Y is hydrogen, lower alkyl, phenyl, or alkoxy to form the phosphinic acid diester of the formula

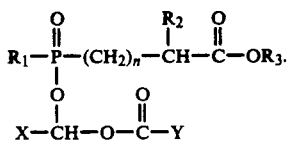

It is disclosed that this reaction is carried out in the presence of an organic base such as triethylamine, which is preferred, pyridine, tripropylamine, diazabicycloundecene or any other common organic bases and an organic solvent such as toluene, which is preferred, acetonitrile, dichloromethane, ethyl ether, tetrahydrofuran, or dioxane and optimally in the presence of a catalyst such as tetrabutylammonium sulfate and sodium iodide.

The resulting phosphinic acid diester is then hydrogenated to form a pair of racemic mixtures which are separated by fractional crystallization to give a single racemic mixture. This racemic mixture is treated with a resolving agent such as L-cinchonidine or other optically active amine to separate out the desired intermediate.

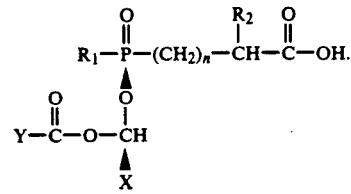

This intermediate wherein $R_1$ is phenylbutyl, n is zero, $R_2$ is hydrogen, Y is ethyl, and X is isopropyl is then coupled to 4-trans-cyclohexyl-L-proline, hydrochloride salt in the presence of a coupling agent to give fosinopril.

SUMMARY OF THE INVENTION

This invention is directed to an improvement in the efficiency of the process for preparing the antihypertensive agent fosinopril and related compounds. According to this improvement, a phosphinic acid ester of the formula

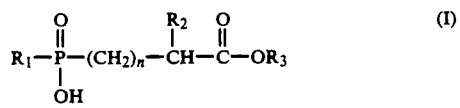

is reacted with a halo ester of the formula

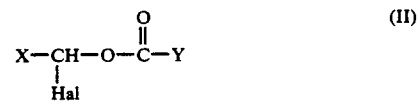

in the presence of 4-methylmorpholine, which is preferred, diazabicyclooctane, quinuclidine, 1-methylpyrolidine, or cinchonidine. The reaction is carried out in organic solvent such as toluene, which is preferred, acetonitrile, dichloromethane, xylene, tetrahydrofuran, or dioxane at a temperature of from about 40° C. to about 138° C., preferably about 95° C., to give a mixture of 4 isomers.

This resulting intermediate is then hydrogenated to remove the $R_3$ ester group by treating with hydrogen in the presence of a catalyst such as palladium on carbon to give a mixture of two diastereomeric pairs. The desired diastereomeric pair contains

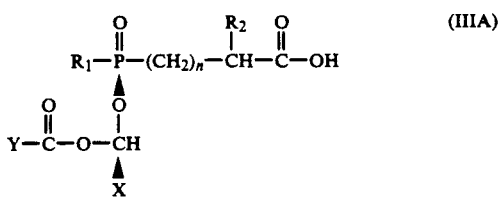

and

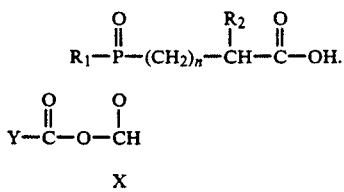

The undesired diastereomeric pair contains

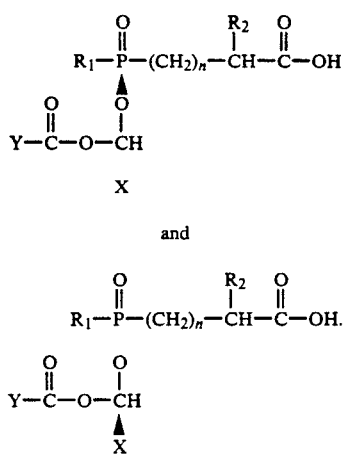

The use of 4-methylmorpholine, diazabicyclooctane, quinuclidine, 1-methylpyrolidine, or cinchonidine in the process results in an increase in the isomer ratio of III A/B to III C/D of from about 1.2 when triethylamine is employed to about 1.5. This increase in the production of desired diastereomeric pair III A/B results in an overall increase in the efficiency of preparing the desired final product.

The symbols used in formulas I to III have the following meanings:

$R_1$ is lower alkyl, cycloalkyl, aryl, aryl-lower alkyl or cycloalkyl-lower alkyl.

n is zero or one.

$R_2$ is hydrogen, lower alkyl, or aryl-lower alkyl.

$R_3$ is

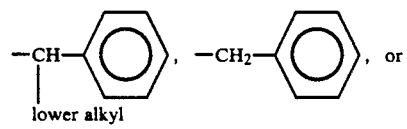

$R_4$ is lower alkyl, lower alkoxy, phenyl,

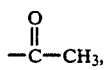

or di(lower alkyl)amino.

X is hydrogen, lower alkyl, or phenyl.

Y is hydrogen, lower alkyl, lower alkoxy or phenyl.

DETAILED DESCRIPTION OF THE INVENTION

The term "lower alkyl" as used throughout this application either by itself or as part of a larger group refers to straight and branched chain groups having 1 to 7 carbon atoms, preferably straight or branched chain of 1 to 4 carbons such as methyl, ethyl, n-propyl, isopropyl, n-butyl, t-butyl, etc.

The term "cycloalkyl" as used throughout this application either by itself or as part of a larger group refers to saturated rings having 3 to 7 carbon atoms, i.e., cyclopropyl, cyclobutyl, cyclopentyl, cyclohexyl, and cycloheptyl.

The term "aryl" as used throughout this application either by itself or as part of a larger group refers to phenyl, 1-naphthyl, or 2-naphthyl, and phenyl, 1-naphthyl, or 2-naphthyl having one, two, or three substituents selected from lower alkyl of 1 to 4 carbons, lower alkoxy of 1 to 4 carbons, lower alkylthio of 1 to 4 carbons, hydroxy, nitro, amino, di(lower alkyl of 1 to 4 carbons) amino, hydroxy, Cl, Br, F, or $CF_3$. Phenyl and monosubstituted phenyl are the preferred aryl groups.

The terms "lower alkoxy" and "lower alkylthio" as used throughout this application refer to such lower alkyl groups attached to an O or S.

The terms "aryl-lower alkyl" and "cycloalkyllower alkyl" as used throughout this specification refer to such aryl and cycloalkyl groups as defined above attached to a lower alkyl group as defined above, i.e.,

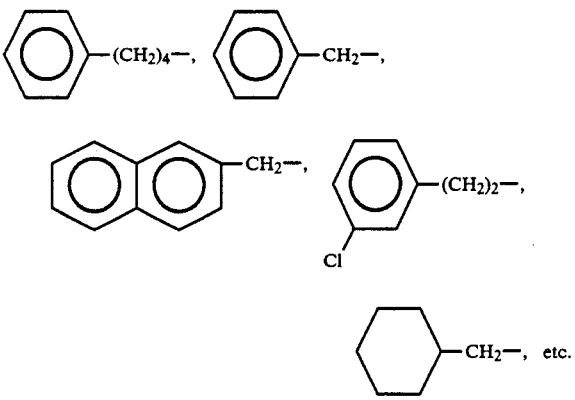

This invention is directed to an improved process for preparing the angiotensin converting enzyme inhibitors disclosed by Petrillo, Jr., in U.S. Pat. Nos. 4,337,201 and 4,384,123. In particular, this invention is directed to an improvement in the preparation of the phosphinate ester IIIa. This ester when $R_1$ is

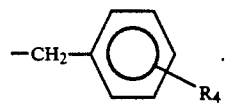

n is zero, $R_2$ is hydrogen, Y is $-C_2H_5$ an X is $-CH(CH_3)_2$ is an intermediate in the preparation of fosinopril.

According to the improved process of this invention, the phosphinic acid ester of formula I particularly wherein $R_3$ is benzyl is reacted with the halo ester of formula II in an organic solvent in the presence of 4-methylmorpholine, diazabicyclooctane, quinuclidine, 1-methylpyrolidine, or cinchonidine and then hydrogenated to remove the $R_3$ ester group and give a mixture of III A, III B, III C, and III D in which the ratio of diastereomeric pair III A/B to III C/D in the mixture is about 1.5.

The phosphinic acid ester I is employed in a molar ratio to the halo ester II within the range from about 0.1:1 to about 1:1 and preferably from about 0.2:1 to 0.3:1 and the reaction is carried out at a temperature of about 40° C. to about 138° C., preferably about 95° C. for a period of from about 18 to about 96 hours.

After removal of the protecting group by hydrogenolysis, the racemic mixture of III A and III B is then treated with a resolving agent such as L-cinchonidine which is preferred or other conventional resolving agent, i.e., an optically active amine, in the presence of an organic solvent such as ethyl acetate, ethyl alcohol, or tetrahydrofuran. This step is carried out at a temperature of from about 25° C. to about 80° C. for about 2 to about 12 hours with the resolving agent being employed in a molar ratio to the racemic mixture of III A and III B in the range of from about 2:1 to about 0.2:1, preferably from about 1:1 to about 0.5:1. The resulting resolved salt of the structure

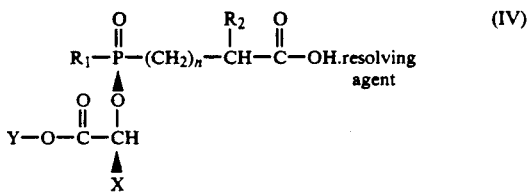

(IV)

is obtained.

Treatment with a strong acid such as hydrochloric or sulfuric acid or an acid salt such as potassium hydrogen sulfate gives III A free from III B.

The resolved acid IIIA wherein $R_1$ is

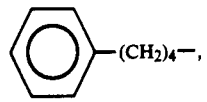

n is zero, $R_2$ is hydrogen, Y is $-C_2H_5$ and X is $-CH(CH_3)_2$ is coupled to the 4-substituted L-proline hydrochloric acid salt of the formula

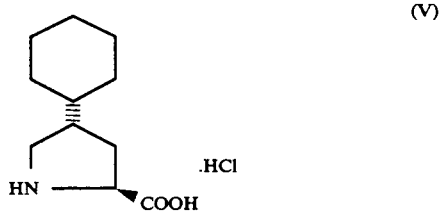

(V)

in the presence of a coupling agent such as N,N'-dicyclohexylcarbodiimide to give fosinopril. Alternatively, the acid of formula IIIA can be converted to an activated form such as a mixed anhydride, acid chloride, etc., and then coupled to the 4-substituted L-proline of formula V or an ester thereof.

The coupling reaction of IIIA and V is carried out employing a molar ratio of IIIA to V of from about 0.5:1 to about 2:1 at a temperature of from about $-20°$ C. to about 30° C. for a period of from about 2 to about 12 hours.

Examples of phosphinic acid ester starting materials of formula I useful in the process of this invention include, but are not limited to:

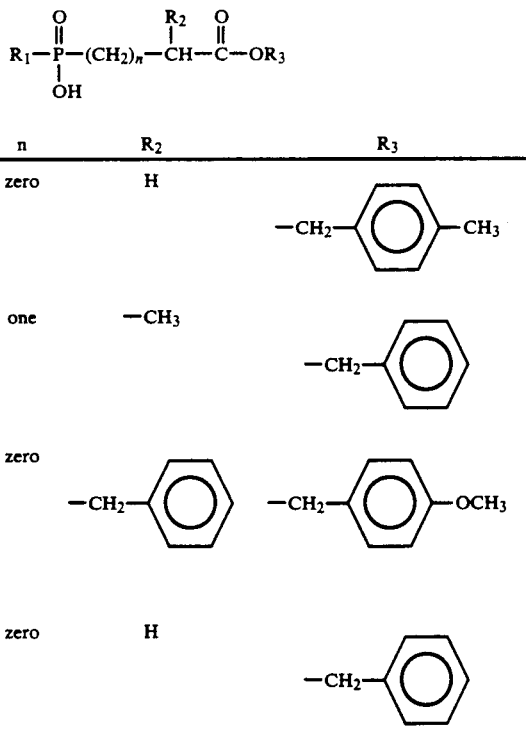

-continued $$R_1-\underset{\underset{OH}{|}}{\overset{\overset{O}{\|}}{P}}-(CH_2)_n-\underset{\underset{}{|}}{\overset{R_2}{C}H}-\overset{\overset{O}{\|}}{C}-OR_3$$

| $R_1$ | n | $R_2$ | $R_3$ |
|---|---|---|---|
| cyclohexyl-$(CH_2)_4$- | one | H | $-\underset{\underset{CH_3}{|}}{CH}-\text{phenyl}$ |
| cyclopentyl- | zero | H | $-CH_2-\text{C}_6H_4-N(CH_3)_2$ |
| $H_3C-H_2C-$ | one | H | $-CH_2-\text{phenyl}$ |

Examples of halo ester starting materials of formula II useful in the process of this invention include, but are not limited to:

$$X-\underset{\underset{hal}{|}}{C}H-O-\overset{\overset{O}{\|}}{C}-Y$$

| X | Y | Hal |
|---|---|---|
| $-CH(CH_3)_2$ | $-CH(CH_3)_2$ | Cl |
| phenyl- | $-C_2H_5$ | Br |
| H | $-OCH_3$ | Cl |
| $-C_2H_5$ | phenyl- | Cl |
| $-CH(CH_3)_2$ | $-C_2H_5$ | Cl |

The following example is illustrative of the invention.

EXAMPLE

[1[S*(R*)],2α,4β]-4-Cyclohexyl-1-[[2-methyl-1-(1-oxopropoxy)propoxy](4-phenylbutyl)phosphinyl]acetyl]-L-proline, monosodium salt (a)
[2-Methyl-1-(1-oxopropoxy)propoxy](4-phenylbutyl)-phosphinyl]acetic acid (diastereomeric pair)

[Hydroxy(4-phenylbutyl)phosphinyl]acetic acid, phenylmethyl ester (100 g., 0.29 mole), 4-methylmorpholine (59.3 g., 0.58 mole) and toluene (150 ml.) were placed in a 500 ml., 3-necked, round-bottomed flask equipped with a stirrer, condenser, and a heating mantle. The mixture was stirred for 15 minutes to insure dissolution.

Propanoic acid, 1-chloro-2-methylpropyl ester (104.6 g., 0.58 mole) was added and the mixture was heated to 95° C. The reaction was stirred at this temperature until the alkylation was determined by HPLC to be completed (18-19 hours).

The solution was cooled to 25° C., vacuum filtered through a sintered glass funnel (medium porosity, 250 ml.) and the 4-methylmorpholine hydrochloride cake was washed with toluene (100 ml., 25° C.).

The filtrate and wash were combined and placed in a 500 ml., 3-necked, round-bottom flask fitted with a gas dispersion tube, mechanical stirrer, condenser, 45° C. water bath and a gas outlet tube. The mixture was stirred at 625 rpm and nitrogen was purged through the solution for 15 minutes.

Palladium on carbon (5%, 2.5 g., dry or 5.0 g. of 50% wet) was added to the solution and hydrogen bubbled through at 1 psi. The hydrogenolysis was complete after 3 hours as determined by HPLC. Nitrogen was purged through the solution to remove excess hydrogen. The solution was filtered over Hyflo (4 g., 7 cm. Buchner Funnel) and the cake was washed with toluene (25 ml.). The combined wash and filtrate were extracted with one portion of aqueous 5% sodium bicarbonate (20 g. of sodium bicarbonate in 380 ml. of water). The aqueous extract was acidified to pH 3.0 with concentrated hydrochloric acid (33 ml.) and extracted with methylisobutyl ketone (400 ml., one extraction). The volume of the methylisobutyl ketone solution was reduced to 200 ml. (40° C. maximum) followed by seeding with the desired diastereomeric pair at 30° C. The slurry was stirred for 2 hours at 30° C. and slowly cooled to 0° C. over 1 hour. The slurry was then cooled to −10° C. After holding at -10° C. for 2 hours, the product was collected by vacuum filtration and washed with cold (-10° C.) methylisobutyl ketone (three 30 ml. portions).

Recrystallization was accomplished by dissolving the product in methylisobutyl ketone (75 ml.) at 70°-80° C. The solution was filtered hot and seeded at 50° with pure product. It was then cooled to 0° over 2 hours. The solution was held at this temperature for 3 hours. The crystals were isolated by vacuum filtration, washed with cold (0°) methylisobutyl ketone (two—30 ml. portions), and air dried for 15 minutes. After drying under vacuum for 16 hours at 26° C., the overall yield of solid [[2-methyl-1-(1-oxopropoxy)propoxy](4-phenylbutyl)-phosphinyl]acetic acid was 49 g. (approximately 44% based upon the average of 3 runs).

Anal. calc'd. $C_{19}H_{29}O_6P$: C, 59.36; H, 7.60; P, 8.06. Found: C, 59.60; H, 7.86; P, 8.07.

(b)
[R-(R*,S*)]-[[2-Methyl-1-(1-oxopropoxy)-propoxy](4-phenylbutyl)phosphinyl]acetic acid To a vigorously stirred suspension of l-cinchonidine (980 g., 3.33 mole) in 6 l. of ethyl acetate maintained at 45° C. was gradually added the diastereomeric product from part (a) (1275.5 g., 3.33 mole) and stirring was continued for an additional 2.5 hours while the resulting suspension of salt was gradually heated to 70° C. when complete solution was obtained. After filtration (Hyflo) from a small amount of insoluble material, the solution was seeded and cooled. The crystalline product which separated was then filtered, washed with 1200 ml., of ethyl acetate:isopropyl ether (1:1), and dried in vacuo to give 1897.2 g. of cinchonidine salt enriched in the desired isomer; m.p. 106°-109° C.; $[\alpha]_D = -59.3°$ (c=1, methanol; $[\alpha]_{365} = -237.6°$ (c =1, methanol). This material was combined with 136.8 g. of similarly prepared material and the total quantity (2014 g.) was recrystallized from 10.18 l. of boiling ethyl acetate to afford after filtration, washing with 1500 ml. of the same solvent mixture used before, and drying in vacuo 1162 g. of desired isomer cinchonidine salt; m.p. 120°-122° (dec.), $[\alpha]_D = -45.2°$ (c=1, methanol); $[\alpha]_{365} = -185.5°$ (c=1, methanol). A sample (10 g.) was recrystallized twice from acetonitrile and three times from ethyl acetate to give an analytical sample of [R-(R*,S*)]-[[2-methyl-1-(1-oxopropoxy)propoxy](4-phenylbutyl)phosphinyl]acetic acid, cinchonidine salt (1:1); m.p. 125°-126° (dec.); $[\alpha]_D = -42.2°$ (c=1, methanol); $[\alpha]_{365} = -178.8°$ (c=1, methanol).

Anal. calc'd. for $C_{19}H_{29}O_6P \cdot C_{19}H_{22}N_2O$: C, 67.23; H, 7.57; N, 4.13. Found: C, 67.17; H, 7.62; N, 4.14.

To a stirred suspension of this cinchonidine salt (406.8 g., 0.6 mole) in a mixture of ethyl acetate (4800 ml.) and water (2700 ml.) was added dropwise a solution of potassium hydrogen sulfate (180 g.) in water (700) to a pH of 2.3. The organic layer was separated, washed with brine (1×1000 ml.) and dried over magnesium sulfate (2 hours). The combined aqueous phases were reextracted with ethyl acetate (3×1500 ml.) and treated as above. The combined ethyl acetate washes were filtered and concentrated in vacuo. The residue was azeotroped with toluene (3×1300 ml.) then dried in vacuo for three days to yield 230.4 g. of [R-(R*,S*)]-[[2-methyl-1-(1-oxopropoxy)propoxy](4-phenylbutyl)-phosphinyl]acetic acid.

(c)
[1[S*(R*)],2α,4β]-4-Cyclohexyl-1-[[[2-methyl-1-(1-oxopropoxy)propoxy](4-phenylbutyl)phosphinyl]acetyl]-L-proline, monosodium salt A slurry of the free acid product from part (b) (230.4 g., 0.6 mole) and hydroxybenzotriazole hydrate, dried in vacuo at 80° C. for 24 hours, (101.1 g., 0.66 mole) in Burdick & Jackson dichloromethane (sieved dried) (6 l.) was chilled in an ice/acetone bath and treated with N,N'-dicyclohexylcarbodiimide (136 g., 0.66 mole). The mixture was warmed to room temperature and stirred for 3 hours. The mixture was then chilled in ice/acetone and treated with (trans)-4-cyclohexyl-L-proline, monohydrochloride salt (154.2 g., 0.66 mole) followed by diisopropylethylamine (170.7 g., 1.32 mole). The reaction mixture was stirred at room temperature for 18 hours. The mixture was then chilled, treated with water (1 l.) and concentrated in vacuo to remove dichloromethane. The residue was diluted with ether (3600 ml.) and water (3600 ml.) and filtered. The filtrate was brought to pH = 1.8 with 10% hydrochloric acid. The ether layer was separated and the aqueous layer washed with ethyl acetate (3×2 l.). The combined organic layers were washed with 5% $KHSO_4$ (3×1 l.), water (3×1 l.) and brine (1 l.), dried over magnesium sulfate and concentrated in vacuo to yield 398.9 g. of crude product.

The crude product was dissolved in acetone (4393 ml.), treated with a solution of 2-ethyl hexanoic acid, sodium salt (117.3 g.) in acetone (1468 ml.), then stirred at room temperature overnight. The resultant precipitate was collected by filtration, washed with acetone (3×400 ml.) and hexane (1 l.) then dried in vacuo to give 277 g. of [1[S*(R*)], 2α, 4β]-4-cyclohexyl-1-[[[2-methyl-1-(1-oxopropoxy)propoxy](4-phenylbutyl)phosphinyl]acetyl]-L-proline, monosodium salt; m.p. 195°-196° C.; $[\alpha]_D = -5.1°$ (c=2, methanol).

Anal calc'd. for $C_{30}H_{45}NO_7P \cdot Na$: C, 61.53; H, 7.75; N, 2.39; P, 5.29. Found: C, 61.69; H, 7.89; N, 2.34; P, 5.1.

What is claimed is:

1. A process for preparing the desired diastereomeric pair containing

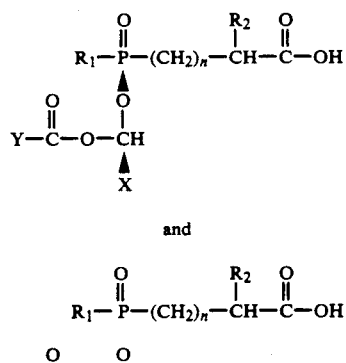

and in increased yield, relative to the undesired diastereomeric pair containing

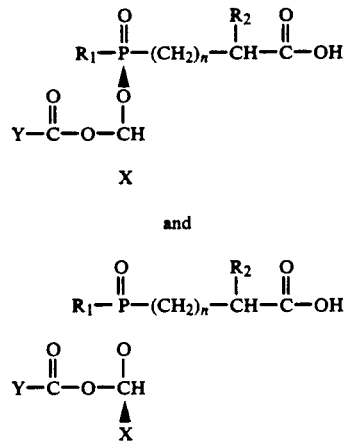

and which comprises
(a) reacting a phosphinic acid ester of the formula

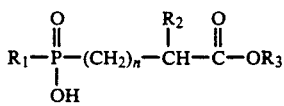

with a halo ester of the formula

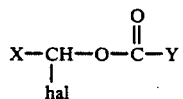

in the presence of 4-methylmorpholine, diazabicyclooctane, quinuclidine, 1-methylpyrolidine, or cinchonidine in an organic solvent at a temperature of about 40° C. to about 138° C. to give an intermediate comprising a mixture of 4 isomers;

(b) hydrogenating the mixture ob 4 isomers from step (a) to remove the $R_3$ ester group and give the desired diastereomeric pair in increased yield from the undesired diastereomeric pair wherein:

$R_1$ is lower alkyl, cycloalkyl, aryl, aryl-lower alkyl, or cycloalkyl-lower alkyl;
n is zero or one;
$R_2$ is hydrogen, lower alkyl, or aryl-lower alkyl;

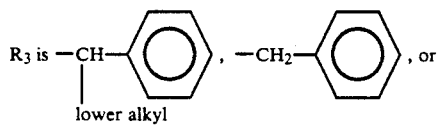

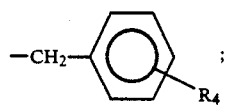

$R_4$ is lower alkyl, lower alkoxy, phenyl,

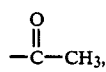

or di(lower alkyl)amino;
Hal is Br or Cl;
X is hydrogen, lower alkyl, or phenyl; and
Y is hydrogen, lower alkyl, lower alkoxy, or phenyl.

2. The process of claim 1 wherein:
$R_1$ is

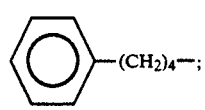

n is zero;
$R_2$ is hydrogen;
Hal is Cl;
$R_3$ is

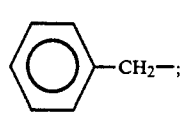

X is —CH(CH$_3$)$_2$; and

Y is —C$_2$H$_5$.

3. The process of claim 2 wherein: the reaction in step (a) is carried out in the presence of 4-methylmorpholine and the ratio of desired diastereomeric pair to undesired diasteromeric pair is about 1.5.

4. the process of claim 3 wherein: the reaction in step (a) is carried out in toluene at a temperature of about 95° C. for from about 18 to 19 hours and the hydrogentation in step (b) is carried out by bubbling hydrogen at 1 psi through the reaction in the presence of palladium on carbon.

5. A process for preparing fosinopril sodium in increased yield comprising (a) reacting a phosphinic acid ester of the formula

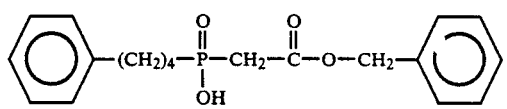

with a halo ester of the formula

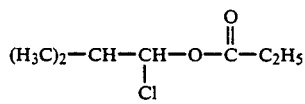

in the presence of 4-methylmorpholine, diazabicyclooctane, quinuclidine, 1-methylpyrolidine, or cinchonidine in an organic solvent at a temperature of about 40° C. to about 138° C. to give an intermediate comprising a mixture of 4 isomers;

(b) hydrogenating the mixture of 4 isomers from step (a) to give an increased yield of the desired diastereomeric pair containing

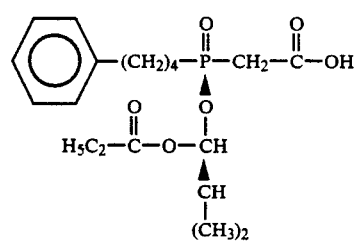

and

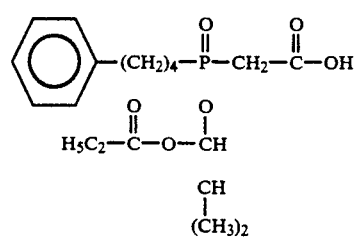

relative to the undesired diastereomeric pair containing

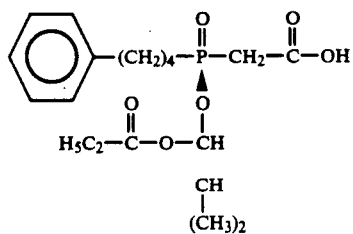

and

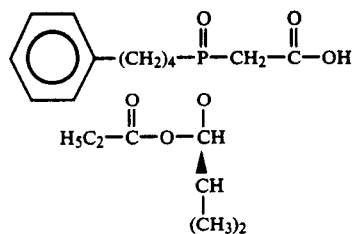

(c) separating the desired diastereomeric pair from the undesired diastereomeric pair in step (b) by extraction with methylisobutyl ketone;

(d) resolving the desired diastereomeric pair from step (c) by treating with an optically active amine to form a salt and treating the salt of the desired isomer with a strong acid or acid salt to give

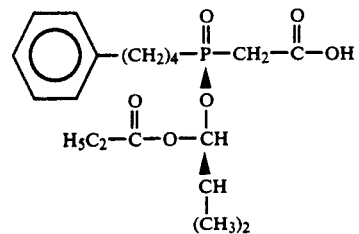

(e) coupling the resolved acid product from step (d) to (trans)-4-cyclohexyl-L-proline, monohydrochloride salt followed by treatment with a source of sodium ions to give fosinopril sodium.

6. The process of claim 5 wherein: the reaction in step (a) is carried out in the presence of 4-methylmorpholine and the ratio of desired diastereomeric pair to undesired diastereomeric pair is about 1.5.

7. The process of claim 6 wherein: the reaction in step (a) is carried out in toluene at a temperature of about 95° C. for about 18 to 19 hours and the hydrogenation in step (b) is carried out by bubbling hydrogen at 1 psi through the reaction in the presence of palladium on carbon.

8. The process of claim 7 wherein: the resolving agent in step (d) is l-cinchonidine.

9. The process of claim 8 wherein the coupling reaction in step (e) is performed in the presence of a coupling agent.

10. The process of claim 9 wherein the coupling agent in step (e) is N,N'-dicyclohexylcarbodiimide and the source of sodium ions is 2-ethyl hexanoic acid, sodium salt.

11. The process of claim 8 wherein the resolved acid product from step (d) is converted to an activated form prior to performance of the coupling reaction in step (e).

* * * * *